US007275539B2

United States Patent
Gippert

(10) Patent No.: US 7,275,539 B2
(45) Date of Patent: Oct. 2, 2007

(54) WICK ARRANGEMENT FOR AN ANESTHETIC EVAPORATOR

(75) Inventor: Karl-Ludwig Gippert, Lübeck (DE)

(73) Assignee: Dräger Medical AG & Co. KGaA (DE)

( * ) Notice: Subject to any disclaimer, the term of this patent is extended or adjusted under 35 U.S.C. 154(b) by 891 days.

(21) Appl. No.: 10/131,716

(22) Filed: Apr. 24, 2002

(65) Prior Publication Data

US 2003/0010476 A1    Jan. 16, 2003

(30) Foreign Application Priority Data

Jul. 13, 2001 (DE) .............................. 101 34 284

(51) Int. Cl.
*A61M 15/00* (2006.01)
*A61M 16/00* (2006.01)
(52) U.S. Cl. .................... 128/204.12; 128/204.14; 128/203.12; 128/203.14; 165/165; 165/907; 165/DIG. 398
(58) Field of Classification Search ........... 165/104.26, 165/165, 902, DIG. 398; 431/326; 128/203.14, 128/204.13, 204.14, 203.12
See application file for complete search history.

(56) References Cited

U.S. PATENT DOCUMENTS

| 3,954,920 A | * | 5/1976 | Heath .................... 261/104 |
| 4,774,032 A | * | 9/1988 | Coates et al. ........... 261/104 |
| 6,325,063 B1 | * | 12/2001 | Volgyesi .............. 128/204.13 |

FOREIGN PATENT DOCUMENTS

| EP | 0 220 258 | 5/1987 |
| GB | 0 220 258 B1 | * 8/1990 |

\* cited by examiner

*Primary Examiner*—Gary L. Welch
*Assistant Examiner*—Nihir Patel
(74) *Attorney, Agent, or Firm*—McGlew & Tuttle P.C.

(57) ABSTRACT

A wick arrangement for an anesthetic evaporator includes a wick with a carrier material (2) that is essentially impermeable to gas provided with wick material (3, 4) on both sides. A great path length is provided for saturating the gas with anesthetic vapor in the smallest possible installation volume by providing flow channels such as helical flow channels (10, 11) extending helically on both sides of the wick. The gas flow is led in counterflow in the flow channels (10, 11) by a housing (9).

20 Claims, 3 Drawing Sheets

WICK ARRANGEMENT FOR AN ANESTHETIC EVAPORATOR

FIELD OF THE INVENTION

The present invention pertains to a wick arrangement for an anesthetic evaporator and more particularly to a wick arrangement for an anesthetic evaporator provided with a wick material.

BACKGROUND OF THE INVENTION

An anesthetic evaporator has been known, in which the a gas flow entering a gas entry pipe branch of the anesthetic evaporator is divided into a so-called bypass gas flow and an evaporator chamber gas flow. The two gas flows are again united at a gas outlet pipe branch. The bypass gas flow returns directly to the gas outlet pipe branch via a bypass line, while the evaporator chamber gas flow is enriched with anesthetic vapor up to the saturation limit in an evaporator chamber. Different anesthetic concentrations can be set by changing the ratio of the two gas flows in relation to one another. Such an anesthetic evaporator has become known from EP 220 258 B1.

A wick, which is rolled up helically, is immersed into liquid anesthetic and through which the gas to be saturated flows from the outside to the inside, is located within the evaporator chamber. The liquid anesthetic rises in the wick by capillary action and is distributed over the entire surface of the wick. The wick surface must be dimensioned to be such that complete saturation of the flow in the evaporator chamber with anesthetic vapor is still reached at the maximum flow through the evaporator chamber. However, a large wick surface leads to a larger evaporator chamber volume in the prior-art anesthetic evaporator. However, not only does a large evaporator chamber volume increase the volume of the anesthetic evaporator, but also has an adverse effect on the necessary constancy of the anesthetic concentration during changes in pressure, which occur during respiration. To compensate this effect of the changes in pressure on the anesthetic concentration released, a so-called pressure compensation line, with which the gas enriched with anesthetic shall be prevented from flowing back into the bypass gas flow, is provided at the inlet of the evaporator chamber. Thus, the pressure compensation line must also be made correspondingly longer in case of a large evaporator chamber volume, which leads to an additional increase in the volume of the anesthetic evaporator.

SUMMARY OF THE INVENTION

The basic object of the present invention is to propose a wick arrangement for an anesthetic evaporator, with which the greatest possible path length is obtained for saturating the gas with anesthetic, with the smallest possible installation volume.

According to the invention a wick arrangement is provided for an anesthetic evaporator with a wick comprising a carrier material which is essentially impermeable to gas and which is provided with wick material on both sides. The wick is provided such that helically extending flow channels are present on both sides of the wick and the wick has deflecting means for the gas flow such that the gas flow is led in counterflow in the flow channels that are located next to one another and are separated by the wick.

According to another aspect of the invention a wick arrangement for an anesthetic evaporator includes a wick in the form of concentrically arranged ring channels which are coated with wick material and have partitions blocking the gas flow and perforations as deflecting or diverting means between the ring channels. The perforations are positioned in relation to the partitions such that reversal of the direction of flow is brought about by the partitions of the ring channels located adjacent to one another at the time of the passage of the gas flow over into a adjacent ring channel.

The advantage of the present invention is essentially that the flow through the wick arrangement takes place in so-called counterflow, so that the wick material can be utilized for enriching the gas flow with anesthetic vapor on both sides of the carrier material. The gas flow now comes into contact first with the wick material of one side of the carrier material and is then sent by a deflecting means to the other side of the carrier material and is further saturated with anesthetic vapor by the wick material present there. Compared with the prior-art wick arrangement with a wick wound helically, through which the flow is from the outside to the inside, the wick arrangement described in the present invention has a flow path that is twice as long and the path available for enriching the gas flow with anesthetic vapor is consequently twice as long as well. Due to the carrier material being coated with wick material on both sides, both sides of the carrier material can be utilized for evaporating the liquid anesthetic. The carrier material is designed such that it does not let through any appreciable gas flow, but the gas flow flows predominantly over the wick material.

The wick material may be permeable to both gas and liquid anesthetic. It preferably consists of a textile fabric or a sintered material. It is also possible to manufacture the wick entirely of a homogeneous material, e.g., a sintered material, which is porous and absorbent on its surface, but is impermeable to gas in the middle because of the greater compaction of the sintered material, so that the passage of gas through the wick is prevented from occurring or at least made difficult. The deflecting means, which deflects the gas flow from one side of the carrier material to the other side, is a baffle plate in the simplest case, with which the gas flow is deflected into the opposite direction of flow.

Since the wick is inserted into the housing of an anesthetic evaporator, the inner wall of the housing may assume the function of the baffle plate.

In an alternative wick arrangement according to the present invention, the wick is designed in the form of concentric ring channels, which are provided with a partition each blocking the gas. To deflect the gas flow, perforations are present in the ring channels, which are positioned in relation to the partitions such that reversal of the direction of flow is brought about by the partitions of the ring channels located adjacent to one another when the gas flow passes over into an adjacent ring channel. Together with the partitions, the perforations form the deflecting means.

Two wick sections formed by turning over the wick are advantageously provided, which are wound helically, where a first flow channel is located between the outer sides of the wick sections, which outer sides face one another, and a second flow channel extends along the inner sides of the wick sections. The flow reversal from the first flow channel into the second flow channel now takes place at the open ends of the wick sections over the inner wall of a housing, into which the wick is placed. If the folded-over end of the wick is located in the middle of an evaporator housing, i.e., if the wick is wound helically around the folded-over end, the gas can be introduced into the wick via the second flow channel in the area of the folded-over end of the wick. The gas will now flow between the wick sections through the second flow channel from the inside to the outside and is then deflected at the inner wall of the evaporator housing into the first flow channel and flows back into the middle in counterflow relative to the direction of flow in the second flow channel and is then fed therefrom as a gas flow enriched with anesthetic vapor to an anesthetic metering means.

To form the flow channels along the wick material, spacers are provided, which are arranged on both sides of the carrier material. The spacer may advantageously also be a coarse-meshed wire mesh, which is placed between the wick material.

The flow channels in a helically wound wick as well as a wick with ring channels may also be formed by designing the wick directly as a helically wound injection molding, so that the flow channels are formed directly by the shaping of the injection molding itself.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
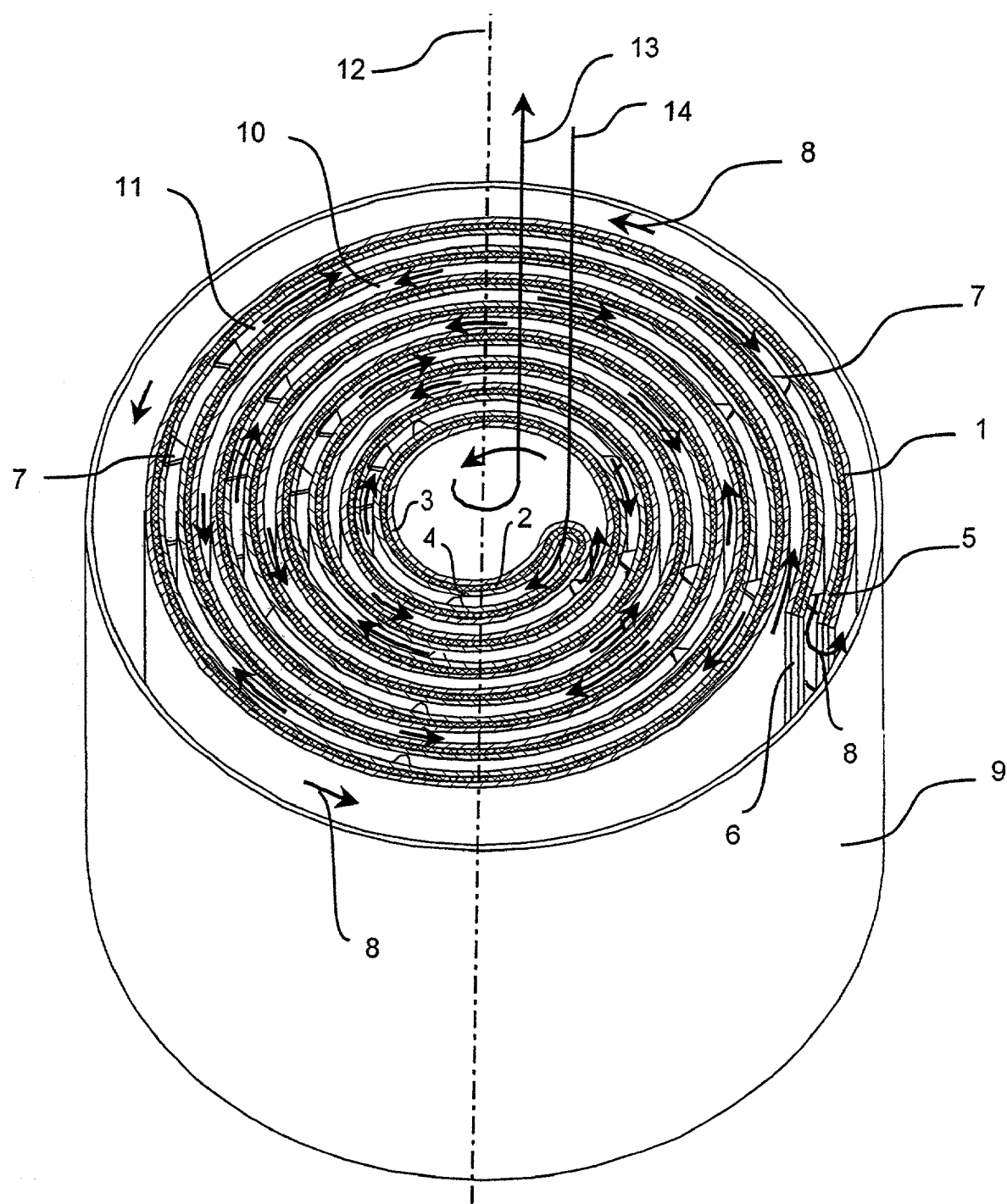
FIG. 1 is a perspective view of a wick with wick sections lying on one another.

Referring to the drawings in particular, FIG. 1 schematically shows a perspective view of a wick 1, which comprises carrier material 2, which is bent over in a U-shaped pattern at a central axis 12 and is provided with wick material 3, 4 on both sides. A first wick section 5 and a second wick section 6, which are of equal size and are flatly in contact with one another, are formed by the folded-over wick 1. The carrier material 2 consists of special steel, while the wick materials are thin, absorbent nonwovens which are connected to the carrier material 2.

The wick 1 is accommodated in a cylindrical housing 9, which is partially filled with a liquid anesthetic, which is not shown in FIG. 1 and is to be evaporated. A first flow channel 10 is formed by the consecutive outer sides of the wick sections 5, 6 with the wick material 3. The inner sides of the wick sections 5, 6 with the wick material 4 form a second flow channel 11. A first gas channel 13 opens into the first flow channel 10 in the area of the central axis 12 of the wick 1, and a second gas channel 14 establishes the flow connection to the second flow channel 11. In the area of the wick 1, the gas channels 13, 14 are provided with openings, not shown specifically in FIG. 1, so that the gas introduced can flow in and out distributed over the wick surface over a large area. The gas flow is illustrated by arrows 8 in FIG. 1, and it extends from the second gas channel 14 into the second flow channel 11 and, after deflections at the inner wall of the housing 9, back into the first flow channel 10, and it flows out of the first flow channel 10 in the area of the central axis 12 into the first flow channel 13. Spacers 7, which are arranged on both sides of the carrier material 2, ensure that free flow is possible in both the first flow channel 10 and the second flow channel 11.

Figure 2:
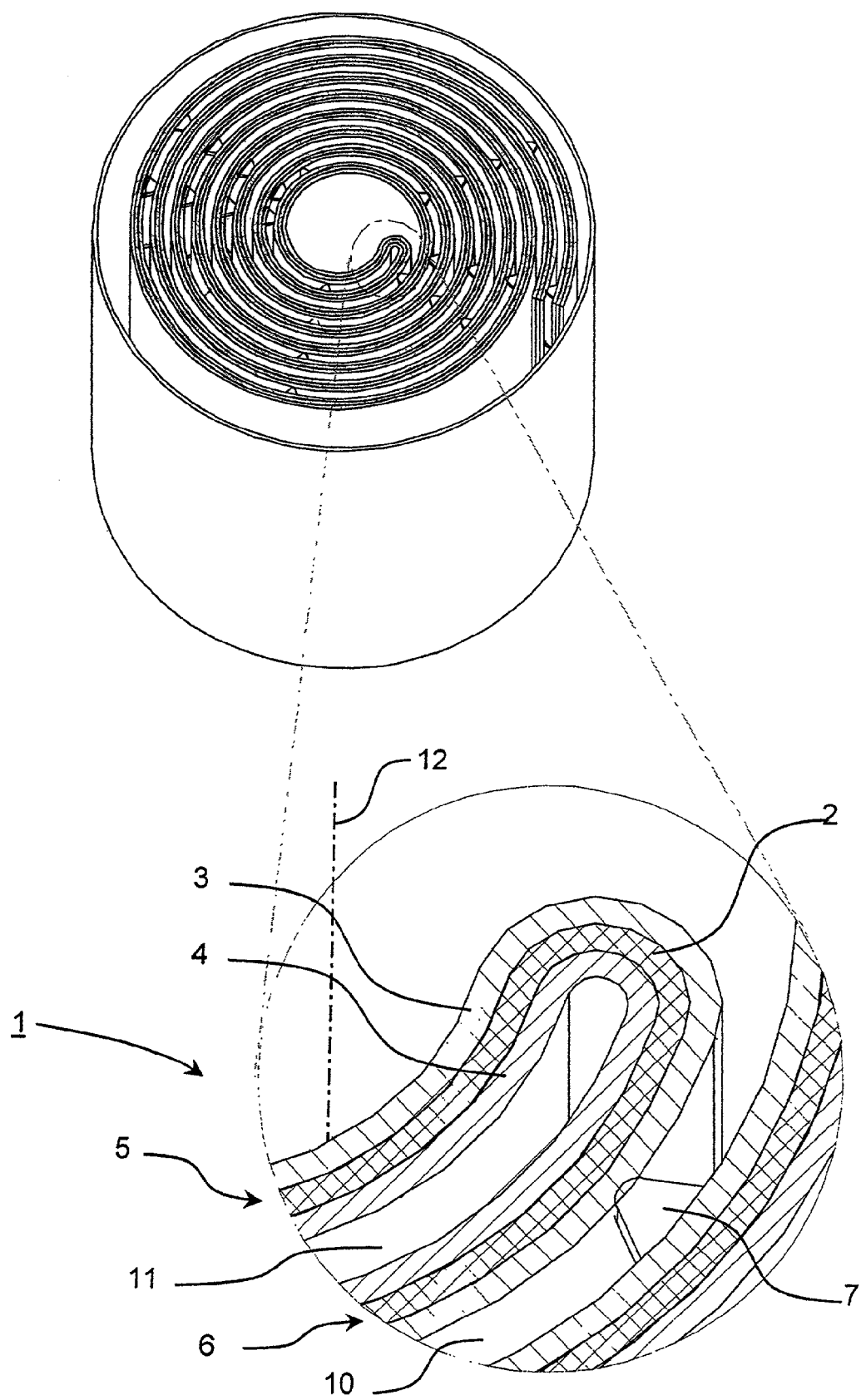
FIG. 2 is a detail in the area of the central axis according to FIG. 1.

FIG. 2 shows an enlarged view of the wick 1 in the area of the central axis 12. The wick sections 5, 6 are formed by folding over the wick 1. Identical components are designated by the same reference numbers as in FIG. 1.

Figure 3:
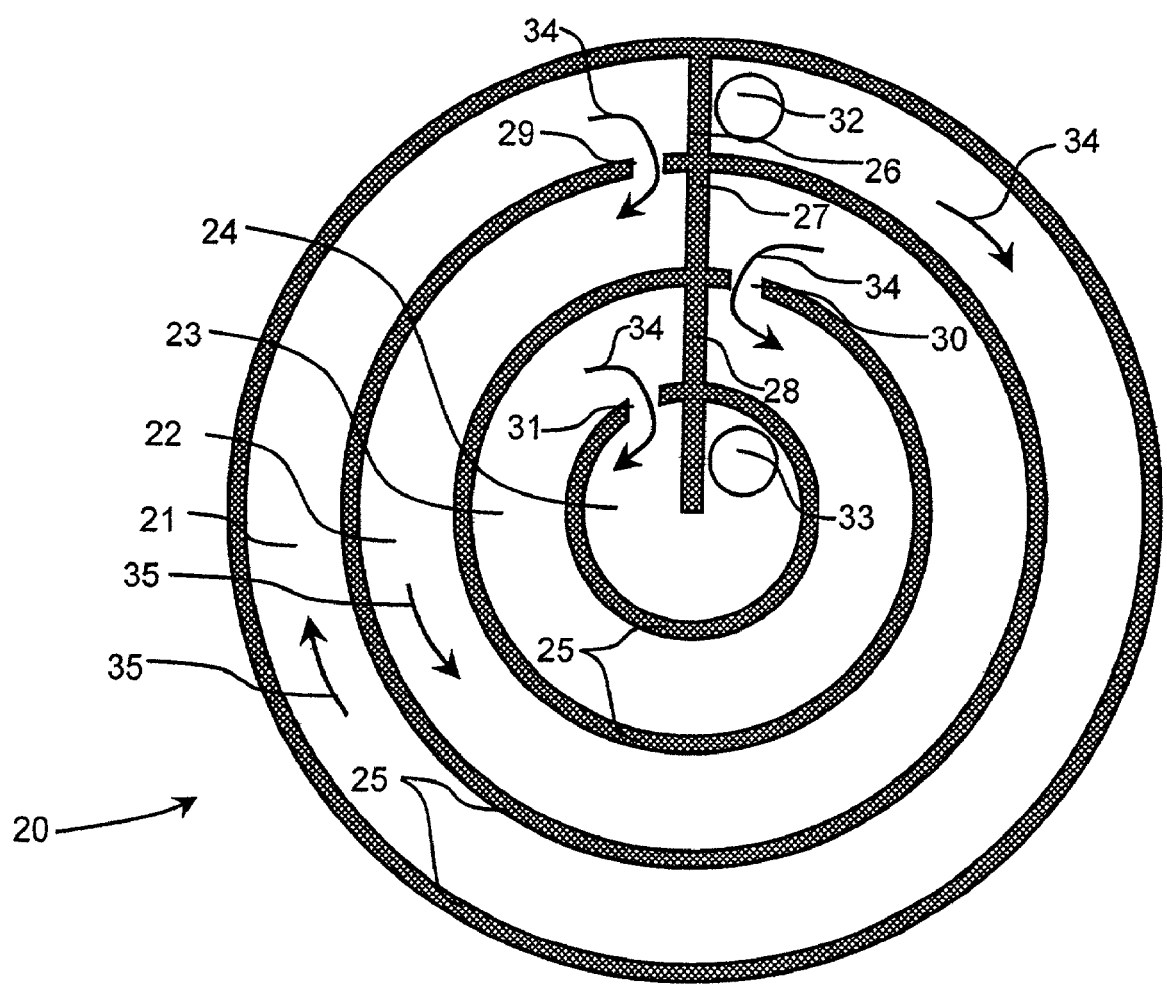
FIG. 3 is a wick arrangement with ring channels.

FIG. 3 schematically shows a top view of a wick arrangement 20, which comprises individual ring channels 21, 22, 23, 24. The walls of the ring channels 21, 22, 23, 24 are formed by a gas-impermeable carrier material, which is coated on both sides with wick material 25, which is not shown specifically in FIG. 3. The ring channels 21, 22, 23, 24 have partitions 26, 27, 28, and perforations 29, 30, 31, with which the gas flow entering the individual ring channels 21, 22, 23, 24 through a flow channel 32 is deflected and leaves a flow channel 33 in the middle. The course of the flow is indicated by arrows 34. The partitions 26, 27, 28, combined with the perforations 29, 30, 31, are used to deflect the gas flow into an adjacent ring channel with reversal of the flow of the gas flow. The gas flows in counterflow in ring channels 21, 22 located next to one another, as is indicated by the arrows 35.

While specific embodiments of the invention have been shown and described in detail to illustrate the application of the principles of the invention, it will be understood that the invention may be embodied otherwise without departing from such principles.

What is claimed is:

1. A wick arrangement for an anesthetic evaporator, the wick arrangement comprising:

a wick comprising a carrier material and wick material on each side of the carrier material, said carrier material being essentially impermeable to gas, said wick being provided with helically extending flow channels on both sides of the wick, the wick having deflecting means for deflecting gas flow such that the gas flow is led in one flow channel in one direction and the gas flow is led in another flow channel in an opposite direction, said flow channels being located adjacent to one another and separated by the wick.

2. A wick arrangement in accordance with claim 1, wherein the wick comprises two wick sections formed by folding over the wick, wherein a first flow channel is located between outer sides of said two wick sections, said outer sides facing one another, and a second flow channel extends along inner sides of said two wick sections and the deflecting means reverses the gas flow between the flow channels and comprises a wall part of the wick at open ends of the wick sections.

3. A wick arrangement in accordance with claim 1, wherein the wick is wound essentially helically.

4. A wick arrangement in accordance with claim 2, wherein the wick is wound essentially helically.

5. A wick arrangement in accordance with claim 1, further comprising spacers provided in the area of the wick material.

6. A wick arrangement in accordance with claim 5, wherein said spacers comprise wide-mesh wire mesh.

7. A wick arrangement in accordance with claim 1, wherein the carrier material for the wick material are formed of a steel sheet or passivated brass plate.

8. A wick arrangement in accordance with claim 1, wherein the wick is an at least partially a helical molding.

9. A wick arrangement for an anesthetic evaporator, the wick arrangement comprising:
 an outer wall;
 carrier material within said outer wall;
 wick material on each side of the carrier material, said carrier material and wick material defining flow channels with wick material on each side; and
 a deflecting means for deflecting gas flow such that the gas flow is led over the wick material on one side of the carrier in one flow channel in one direction and the gas flow is led over the wick material on the other side of the carrier in another adjacent flow channel in another direction.

10. A wick arrangement in accordance with claim 9, wherein a single carrier material element is provided with said wick material on each side to form a wick that is folded over to form two wick sections wherein a first flow channel is located between outer sides of said two wick sections, said outer sides facing one another, and a second flow channel extends along inner sides of said two wick sections and said deflecting means reverses the gas flow between the flow channels and comprises a portion of the wick at open ends of the wick sections.

11. A wick arrangement in accordance with claim 10, wherein the wick is wound essentially helically.

12. A wick arrangement in accordance with claim 10, further comprising spacers provided in the area of the wick material.

13. A wick arrangement in accordance with claim 12, wherein said spacers comprise wide-mesh wire mesh.

14. A wick arrangement in accordance with claim 10, wherein the wick is at least partially a helical molding.

15. A wick arrangement in accordance with claim 10, wherein the rings are formed of a steel sheet or passivated brass plate.

16. A wick arrangement in accordance with claim 9, wherein said carrier material comprises concentrically arranged rings coated with said wick material to form ring channels, said deflecting structure including partitions blocking gas flow in said channels and perforations in at least some of said ring channels with said perforations being positioned in relation to the partitions such that reversal of the direction of flow is brought about by the partitions located adjacent to one another upon passage of the gas flow over into an adjacent ring channel.

17. A wick and housing arrangement for an anesthetic evaporator, the wick and housing arrangement comprising:
 an outer wall defining a housing;
 a first gas channel for leading a gas flow out of said housing;
 a second gas channel for leading a gas flow into said housing;
 carrier material within said outer wall;
 wick material on each side of the carrier material, said carrier material and wick material defining a first flow channel supplying the gas flow to said first gas channel and defining a second flow channel for receiving the gas flow from said second gas channel, said first flow channel being between portions of said second flow channel and said second flow channel being between portions of said first flow channel;
 a deflecting means for deflecting gas flow from said second flow channel to said first flow channel such that the gas flow is led over the wick material in said second flow channel traveling in one direction and the gas flow is led over the wick material in said first flow channel traveling in an opposite direction.

18. A wick arrangement in accordance with claim 17, wherein a single carrier material element is provided with said wick material on each side to form a wick that is folded over to form two wick sections wherein said first flow channel is located between inner sides of said two wick sections, said inner sides facing one another, and said second flow channel extends along outer sides of said two wick sections and said deflecting means reverses the gas flow between the flow channels and comprises open ends of the wick sections and an inner side of said outer wall.

19. A wick arrangement in accordance with claim 18, further comprising spacers provided in the area of the wick material.

20. A wick arrangement in accordance with claim 17, wherein said carrier material comprises concentrically arranged rings coated with said wick material to form said first flow channel and said second flow channel, said deflecting means including partitions blocking gas flow in said channels and perforations in at least some of said ring channels with said perforations being positioned in relation to the partitions such that reversal of the direction of flow is brought about by the partitions located adjacent to one another upon passage of the gas flow over into an adjacent ring channel.

* * * * *